United States Patent [19]

McHale et al.

[11] E Patent Number: Re. 31,647

[45] Reissued Date of Patent: Aug. 14, 1984

[54] STARTUP PROCEDURE FOR REFORMING CATALYSTS

[75] Inventors: William D. McHale, Mantua; Hans J. Schoennagel, Lawrenceville, both of N.J.

[73] Assignee: Mobil Oil Corporation, New York, N.Y.

[21] Appl. No.: 382,515

[22] Filed: May 27, 1982

Related U.S. Patent Documents

Reissue of:

[64] Patent No.: 4,261,810
Issued: Apr. 14, 1981
Appl. No.: 130,802
Filed: Mar. 17, 1980

[51] Int. Cl.[3] ..... C07C 35/08

[52] U.S. Cl. ..... 208/138; 208/139; 585/906; 585/951

[58] Field of Search ..... 208/138, 139; 585/951, 585/906

[56] References Cited

U.S. PATENT DOCUMENTS

| | | | |
|---|---|---|---|
| 2,848,377 | 8/1958 | Webb | 208/139 |
| 2,885,351 | 5/1959 | Johnston, Jr. | 208/138 |
| 3,415,737 | 12/1968 | Kluksdahl | 208/138 |
| 3,438,888 | 4/1969 | Spurlock | 208/138 |
| 3,487,009 | 12/1969 | Jacobson et al. | 208/138 |
| 3,507,781 | 4/1970 | Spurlock et al. | 208/138 |
| 3,953,368 | 4/1976 | Sinfelt et al. | 208/139 |
| 4,148,758 | 4/1979 | Eberly | 208/139 |
| 4,149,962 | 4/1979 | Antos | 208/139 |

FOREIGN PATENT DOCUMENTS

| | | |
|---|---|---|
| 2627822 | 2/1977 | Fed. Rep. of Germany . |
| 1160258 | 8/1969 | United Kingdom . |
| 1560368 | 2/1980 | United Kingdom . |
| 2028158 | 3/1980 | United Kingdom . |

*Primary Examiner*—Curtis R. Davis
*Attorney, Agent, or Firm*—Charles A. Huggett; Michael G. Gilman; Stanislaus Aksman

[57] ABSTRACT

Process for reforming a hydrocarbon charge under reforming conditions in a reforming zone containing a sulfur-sensitive metal containing reforming catalyst wherein over-cracking of the charge stock and excessive temperature rise in the reforming zone is suppressed by pre-conditioning the catalyst, prior to contact with the charge, with a reformate of specified octane number and aromatics content.

27 Claims, 3 Drawing Figures

STARTUP PROCEDURE FOR REFORMING CATALYSTS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a catalytic reforming process wherein a suitable charge stock, such as a petroleum naphtha, is converted to a gasoline of high octane number. More particularly, the invention described herein is concerned with a startup procedure for treating a metal-containing reforming catalyst, normally sulfur-sensitive under conventional conditions of reforming operation.

2. Description of the Prior Art

Catalysts intended for use in reforming processes wherein hydrocarbon fractions, e.g., naphthas or gasoline or mixtures thereof are converted to improve the anti-knock characteristics thereof are well known in the petroleum industry.

It has heretofore been proposed to employ metal-containing catalysts, notably those containing a platinum metal, for promoting reforming. Such catalysts are necessarily characterized by a certain amount of acidity. One type of reforming catalyst which has been used commercially consists of an alumina base material having platinum metal impregnated thereon, with the acidity characteristics being contributed by a small amount of halogen incorporated in the catalyst.

In more recent years, multimetallic reforming catalysts, for example, bimetallic catalysts, have come into use. These catalysts generally contain platinum, together with one or more additional metals such as rhenium, germanium, iridium, palladium, osmium, ruthenium, rhodium, copper, silver, tin or gold deposited on a refractory support which also contains a specified amount of halogen. Representative of multimetallic reforming catalysts are those containing platinum and rhenium, such as described in U.S. Pat. No. 3,415,737; those containing platinum and iridium, such as described in U.S. Pat. Nos. 2,848,377 and 3,953,368 and those containing platinum, rhenium and iridium such as described in U.S. Pat. No. 3,487,009.

Reforming generally initially produces an excessive amount of light gases, e.g., methane and ethane, unless proper pretreatment or startup procedures are utilized. The light hydrocarbon gases, produces as a result of high hydrocracking activity or metal-cracking activity of the catalyst, are particularly to be avoided during reforming since they serve to decrease the yield of gasoline boiling products. It is known that hydrocracking activity can be diminished if the catalyst is sulfided prior to contact with the charge stock. The presulfiding can be accomplished, for example, by passing a sulfur-containing gas e.g., $H_2S$, through the catalyst bed. Other presulfiding treatments utilizing various other sulfur-containing compounds are known from prior art, such as U.S. Pat. No. 3,415,737.

While generally any of the aforenoted metal-containing reforming catalysts are adversely affected by the presence of an excess amount of sulfur, i.e., greater than about 15 ppm, those in which iridium is a catalytically active component are known to be extremely sensitive to the presence of sulfur. Thus, it has been reported, for example, in U.S. Pat. No. 3,507,781, that reforming catalysts comprising catalytically active amounts of platinum and iridium supported on a porous solid carrier, for example, alumina, are extremely sensitive to sulfur concentrations, exceeding about 2 ppm. At such concentrations, the increase in catalyst temperature necessary to maintain conversion of the chargestock to a constant octane number gasoline product increases very substantially.

During the startup period of a reforming unit, utilizing a metal, e.g., a platinum-iridium-containing catalyst, that is, when the catalyst is initially or immediately after regeneration contacted with hydrogen and naphtha at reforming conditions, the catalyst causes excessive hydrocracking which has been termed "hydrogenolysis". As a consequence of such high hydrocracking activity, an excessive temperature rise or heat front, travels through the catalyst as naphtha is initially contacted with the catalyst in the presence of hydrogen and at reforming conditions. Although the occurring temperature rise only exists in the initial period of contact with the naphtha feed, such could be the cause of a temperature runaway in a commercial reforming plant. The temperatures in the bed may increase as high as several hundred degrees above the temperature of the naphtha introduced to the reaction zone. Obviously, such a severe temperature increase can damage the reactor and/or catalyst and is to be strictly avoided.

One method of controlling the hydrocracking activity of the platinum-containing reforming catalyst, e.g., platinum in combination with iridium and/or rhenium catalyst, would be to add a quantity of sulfur to the feed during the startup period. However, such catalyst, as indicated above, is very sensitive to the presence of sulfur and other means of control have accordingly been sought.

One alternative suggested method is that described in U.S. Pat. No. 3,507,781 wherein a reforming process using a catalyst containing platinum and iridium on a porous solid carrier is started up by contacting the naphtha with the catalyst in the presence of an inert gas, for example, nitrogen. Utilizing such technique, it has been indicated that the pressure in the reforming zone should be about 200 psig and the catalyst temperature about 650° F. when the naphtha is first contacted with the catalyst at a space velocity of about 1 volume/volume/hour. Thereafter, the temperature is increased to about 900° F. over a 2–3 hour period while building up autogeneous pressure of produced hydrogen.

Another method is that described in U.S. Pat. No. 4,148,758 wherein excessive hydrocracking or hydrogenolysis of a sulfur sensitive reforming catalyst is suppressed by incorporating within the reforming catalyst at the time of its preparation a sulfurous acid or sulfuric acid component.

Such prior suggested alternative techniques have had the disadvantage of requiring extremely careful control of treating conditions or with respect to the method described in the latter patent the use of corrosive chemicals.

SUMMARY OF THE INVENTION

In accordance with the invention described herein, it has been found that temperature runaways in the catalytic reforming unit and overcracking of the chargestock, i.e., hydrogenolysis, can be very substantially reduced or even completely eliminated, when the metal-containing reforming catalyst, during initial use or in a freshly regenerated state, is contacted in a preliminary step, prior to contact with the chargestock, with a reformate characterized by an octane number (R+O) between about 90 and about 100 and an aromatics content within the approximate range of 40 to 50 mole percent for a specified period of time, generally at least about 0.5 hour and not more than about 3 hours at a temperature between about 600° F. and about 750° F. and preferably between about 650° F. and about 700° F.

After such pretreatment of the catalyst, chargestock, i.e., naphtha, may be admitted to the unit as in a normal startup. It has been found that the procedure of this invention serves to limit temperature increases to insignificant levels, generally not in excess of about 30° F., while maintaining the maximum activity and selectivity. In contrast, the temperature of a comparable reforming catalyst increased from 650° F. to 1300° F. in one minute when normal $C_6$-330° F. charge naphtha was passed over the catalyst.

It is contemplated that metal-containing reforming catalysts, normally sensitive to sulfur, may be beneficially affected by the startup procedure of the invention described herein. Thus, while Group VIII noble metal supported reforming catalysts, e.g., platinum on alumina, may be advantageously treated utilizing the startup procedure described herein, the latter is particularly applicable for and treatment of multi-metallic catalysts, e.g., platinum-rhenium, platinum-iridium and platinum-rhenium-iridium, particularly fresh or regenerated reactivated catalysts of such type, which are known to be especially sensitive to sulfur.

The reforming catalyst undergoing treatment in accordance with the startup procedure of the invention generally comprises a Group VIII noble metal component, notably platinum in concentrations ranging from about 0.01 to about 3 percent, based on the weight of the catalyst, a component comprised of iridium or rhenium, or both, in concentration ranging from about 0.01 to about 3 percent, based on the weight of the catalyst and a halogen component in concentration ranging from about 0.1 to about 3 percent, based on the weight of the catalyst.

Reforming, utilizing the described catalyst, is conducted in the presence of hydrogen under reforming conditions. The latter include a temperature between about 700° F. and 1100° F. and more usually between about 800° F. and about 1000° F.; a pressure within the range of about 50 to about 1000 psig and preferably between about 100 and 700 psig and a liquid hourly space velocity of between about 0.1 and about 10 and preferably about 0.5 and about 4. The molar ratio of hydrogen to hydrocarbon charge is generally between about 0.5 and about 20 and preferably between about 2 and about 12.

The startup technique, constituting the subject matter of this invention, is particularly directed to avoiding temperature runaways in the reforming unit and overcracking of the chargestock without paying a penalty in irreversible activity loss. The procedure involved is economically attractive and does not entail the use of or introduction into the catalyst or reforming system of additional extraneous chemicals. The new startup procedure simply involves exposure of the catalyst to reformate at a temperature within the approximate range of 600° to 750° F. for a period of time followed by incremental replacement of the reformate with increasing amounts of charge naphtha until all the reformate has been replaced. Once this has been achieved and the bed temperatures of the reactors have equilibrated, the startup is capable of proceeding, with avoidance of catalyst presulfiding, in a conventional manner.

DESCRIPTION OF SPECIFIC EMBODIMENTS

Figure 1:
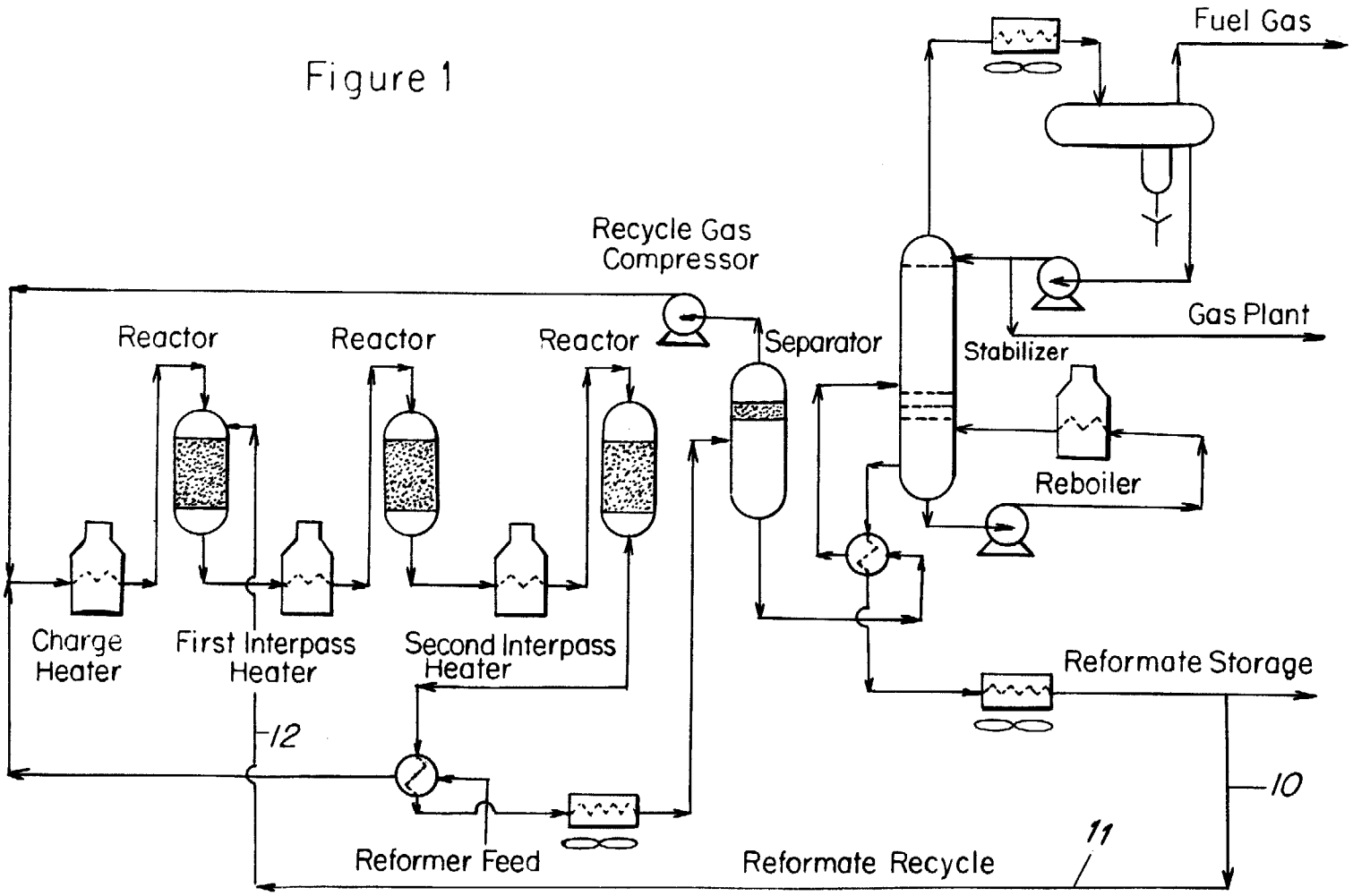
FIG. 1 depicts a catalytic reforming unit wherein a portion of the reformate produced is recycled for preconditioning the catalyst during startup.

Chargestocks undergoing reforming, in accordance with the process described herein, are contemplated, as those conventionally employed. These include virgin naphtha, cracked naphtha, gasoline, including FCC gasoline or mixtures thereof boiling within the approximate range of 70° to 500° F. and, preferably within the range of about 120° to about 450° F. The charge should be essentially free; that is, the feed should contain less than about 10 ppm sulfur and preferably less than 5 ppm and still more preferably less than 1 ppm. The presence of sulfur in the charge decreases the activity of the catalyst as well its stability.

In instances where the chargestock is not already low in sulfur, acceptable levels can be reached by hydrogenating the chargestock in a pretreatment zone wherein the chargestock is contacted with a hydrogenation catalyst which is resistant to sulfur poisoning. A suitable catalyst for this hydrodesulfurization process, is, for example, an alumina-containing support and a minor proportion of molybdenum oxide and cobalt oxide. Such hydrodesulfurization is ordinarily accomplished at 700°-850° F. at 200 to 2000 psig and at a liquid hourly space velocity of 1 to 5. The sulfur contained in the chargestock is converted to hydrogen sulfide, which can be removed by suitable conventional methods prior to reforming.

In a preferred embodiment, hydrogen production and hydrogen purity are maximized while localized hydrocracking and methane production are minimized by inclusion in the reformate of a small amount not exceeding about 10 ppm, of sulfur and maintaining contact between the catalyst and such sulfur-containing reformate until the bed temperatures line out. Charge naphtha, which is thereafter substituted for the reformate, preferably contains about 2 to about 10 ppm of sulfur and particularly preferred about 4 to about 8 ppm of sulfur. Charge naphtha with such sulfur level or with sulfur additives to this level is preferably employed while the inlet temperatures are gradually increased to operating conditions. The time during which the catalyst is exposed to the above treatment is generally in the approximate range of 5 to 24 hours.

After such exposure time, the sulfur can either be withdrawn completely or reduced to a lower level, not exceeding about 2 ppm. This method of streaming a catalyst is superior to presulfiding since it is much more selective. The utilization of the above procedure results in bringing on stream, a catalyst with near optimum activity, yield and hydrogen production and purity in a reliable and reproducible manner.

The reforming catalysts employed are contemplated as being those Group VIII metal-containing, e.g., platinum, catalysts normally sensitive to sulfur under conditions encountered in reforming, and, as aforenoted, particularly multimetallic catalysts containing in addition to platinum, iridium and/or rhenium. Such catalysts may be made by conventional well known techniques in which the metal components are deposited on a single suitable refractory support. Also, reforming catalysts may be used wherein a minor proportion of platinum is deposited on one support and a minor proportion of another metal, such as iridium, is deposited on a separate support. The latter type reforming catalysts are more particularly described in copending application Ser. No. 076,047, filed Sept. 17, 1979.

When the reforming catalyst is made up of separate particles containing platinum or platinum-rhenium and those containing a second metal, e.g., iridium, the relative weight ratio of the separate particles is generally between about 10:1 and about 1:10. The dimensions of the separate particles may range from powder size, e.g., 0.01 micron up to particles of substantial size, e.g., 3000 microns. Preferably, the particle size is between about 1 and about 100 microns.

The refractory support is contemplated as being an inorganic oxide and usually alumina, of the gamma or eta variety. Halogen may be chlorine, bromine or fluorine, with particular preference being accorded chlorine.

Generally, the refractory support of the catalyst is a porous adsorptive material having a surface area exceeding 20 square meters per gram and preferably greater than about 100 square meters per gram. Refractory inorganic oxides are preferred supports, particularly alumina or mixtures thereof with silica. Alumina is particularly preferred and may be usedin a large variety of forms including alumina, precipitate or gel, alumina monohydrate, sintered alumina and the like. Various forms of alumina either singly or in combination, such as eta, chi, gamma, theta, delta or alpha alumina may be suitably employed as the alumina support. Preferably, the alumina is gamma alumina and/or eta alumina. The above nomenclature used in the present specification and claims with reference to alumina phase designation is that generally employed in the United States and described in "The Alumina Industry: Aluminum and its Production" by Edwards, Frary and Jeffries, published by McGraw-Hill (1930).

Halogen may be added to the support, preferably alumina, in a form which will readily react therewith in order to obtain the desired results. One feasible method of adding the halogen is in the form of an acid, such as hydrogen fluoride, hydrogen bromide, hydrogen chloride and/or hydrogen iodide. Other suitable sources of halogen include salts, such as ammonium fluoride, ammonium chloride and the like. When such salts are used, the ammonium ions will be removed during subsequent heating of the catalyst. Halogen may also be added as fluorine, chlorine, bromine or iodine or by treatment in gaseous hydrogen halide. The halogen, preferably a chlorine or fluorine moiety, may be incorporated into the catalyst at any suitable stage in the catalyst manufacture. Thus, halogen may be added before, after or during incorporation of the platinum or platinum-rhenium and iridium on the refractory support. Halogen is conveniently incorporated into the catalyst when impregnating the support with halogen-containing metal compounds, such as chloroplatinic acid and chloroiridic acid. Additional amounts of halogen may be incorporated in the catalyst by contacting it with materials, such as hydrogen fluoride and hydrogen chloride, either prior to or subsequent to the metal impregnation step. Halogen may also be incorporated by contacting the catalyst with a gaseous stream containing the halogen, such as chlorine or hydrogen chloride. One feasible way to halogenate the alumina is by the addition of an alkyl halide, such as tertiary butyl chloride during the reforming operation. The amount of halogen introduced into the support is such that the halogen content of the overall catalyst is between about 0.1 and about 5 weight percent.

The platinum metal may be deposited on the support, desirably alumina, in any suitable manner. Generally, it is feasible to mix particles of support with a platinum compound such as chloroplatinic acid, platinum tetrachloride, bromoplatinic acid, or the ammonium salt of chloroplatinic or bromoplatinic acid.

The iridium metal may be deposited on the support, desirably alumina, by contacting with an appropriate iridium compound such as the ammonium chloride double salt, tribromide, tetrachloride or chloroiridic acid. Iridium amine complexes may also suitably be employed.

The impregnated particles may then be dried in air at an elevated temperature generally not exceeding 250° C. prior to introduction of the catalyst into the reforming unit. Optionally, the catalyst may be exposed to a hydrogen atmosphere to reduce a substantial portion of the platinum component to the elemental state.

It is to be noted that the catalyst of the present invention may contain in addition to platinum, iridium and/or rhenium one of several additional catalytic components such as silver, osmium, copper, gold, palladium, rhodium, gallium, germanium or tin or compounds thereof. The amounts of the added catalytic components may be in the approximate range of 0.01 to 2 weight percent, preferably between about 0.1 and about 1.0 weight percent. The platinum content, rhenium content, iridium content and halogen content of catalysts is in the same range as set forth hereinabove, with the preferred support being alumina.

In a typical commercial reforming process, reaction temperature is increased during the course of the run to maintain a constant product octane level. Increasing the reaction temperature becomes necessary since the catalyst is continuously deactivated. Generally, the reaction temperature cannot exceed about 1000° F. before rapid deactivation of the catalyst is encountered. Accordingly, as the reaction temperature approaches about 1000° F., it is usually necessary to regenerate the catalyst. Regeneration is accomplished by burning the coke deposit from the catalyst and then treating with chloride, HCl-oxygen mixtures or organic chloride-oxygen mixtures to rejuvenate the catalyst and thereby restore its activity and selectivity.

It is contemplated that the catalyst described hereinabove may be employed in any of the conventional types of processing equipment. Thus, the catalyst may be used in the form of pills, pellets, extrudates, spheres, granules, broken fragments or various other shapes dispersed as a fixed bed within a reaction zone. The charge stock may be passed through the catalyst bed as a liquid, vapor or mixed phase in either upward or downward flow. The catalyst may also be used in a form suitable for moving beds. In such instances, the chargestock and catalyst are contacted in a reforming zone wherein the chargestock may be passed in concurrent or countercurrent flow to the catalyst. Alternatively, a suspension-type process may be employed in which the catalyst is slurried in the chargestock and the resulting mixture conveyed to the reaction zone. The reforming process is generally carried out in a series of several reactors. Usually, three to five reactors are used. The catalyst of the invention may be employed in just one of the reactors, e.g., the first reactor or in several reactors or in all reactors. After reaction, the product from any of the above processes is separated from the catalyst by known techniques and conducted to distillation column where the various desired components are obtained by fractionation.

A typical catalytic reforming unit is shown in FIG. 1. Referring more particularly to this Figure, reformer feed, constituting desulfurized naphtha is combined with hydrogen recycle gas, heated and reformed over catalyst contained in the three reactors. Heat is adsorbed during the reforming reactions which requires the stream to be reheated in the first and second interpass heaters. Upon exiting the last reactor the effluent is cooled then split in a fresh separator, after which some of the recycled gas is returned to the unit. The product is stabilized to the desired vapor pressure and the reformate obtained as part of the motor gasoline or aviation fuel pool. The vapor effluent from the last reactor of the series is a gas rich in hydrogen, which usually contains small amounts of gaseous hydrocarbons and is separated from the $C_{5+}$ liquid product and recycled to the process to minimize coke production, which forms and deposits on the catalyst during the reaction.

In one embodiment of the present invention, a stream of reformate produced is recycled in the overall catalytic reforming system shown in FIG. 1, through lines 10, 11 and 12 to the first reforming reactor, where it serves, in accordance with the desired startup procedure to pre-condition the catalyst preliminary to further contact with reformer charge stock. It will be understood that the reformate recycle stream is controlled in amount and maintains contact with the catalyst undergoing treatment for a desired period of time by means of suitable valve controls, which, for purposes of simplicity, have been omitted from the drawing. Also, it will be understood that during the period of pre-conditioning of the catalyst by contact with the reformate recycle stream, the flow or reformer charge stock is discontinued to the inital reforming reactor by suiutable control means.

The following examples will serve to illustrate the start up procedure of this invention without limiting the same.

EXAMPLE 1

One hundred (100) grams of gamma-alumina beads were impregnated by soaking overnight in 145 ml of aqueous hexachloroplatinic acid solution containing 0.6 gram of platinum. By the following day, the support had adsorbed the aqueous solution, including the platinum. The catalyst was then dried overnight at 110° C. in air. Similarly, the iridium component was made by impregnating 62.2 grams of gamma-alumina beads with 90 ml of a solution containing 1 gram of $H_2IrCl_6.6H_2O$ (37.3 weight percent Ir). Following adsorption of this solution by the support, the iridium containing component was dried at 110° C. overnight in air. Finally, the catalyst consisting of 0.3 wt. % platinum and 0.3 wt. % iridium was made by mixing equal amounts of the 0.6 wt. % platinum and 0.6 wt. % iridium catlayst.

EXAMPLE 2

The catalyst of Example 1 was presulifided with hydrogen containing 400 ppm of hydrogen sulfide. The catalyst was apportioned as follows: 12 grams—first reactor, 22 grams—second reactor and 25 grams—third reactor. With the catalyst at 750° F., 200 psig and the recycle at 6 standard cubic feet per hour, the presulfiding gas was put into the first of three reactors in series for one hour (2.0055 cu. ft.). Breakthrough was not detected after the last reactor. Following this, charge naphtha was pumped at 190 ml/hour with 10 ml/hour of 1% tert.-butyl chloride in naphtha for 200 minutes. The 1% solution of ter.-butyl chloride was then replaced with a solution containing 1500 cc of naphtha and 30 cc of 1% tert.-butyl chloride in naphtha and the catalyst was on stream.

EXAMPLE 3

The catalyst of Example 1 was pretreated at 650° F., 100 psig and recycle of 10 standard cubic feet per hour with 98 R+O reformate. The catalyst was loaded with 9 grams in the first reactor, 17 grams in the second reactor and 19 grams in the third reactor. Initially, 76 ml/hr of promoter I, composed of 1 gram tert.-butyl chloride in 130 grams of 98 R+O reformate, was pumped for 20 minutes. This was then replaced with promoter II, composed of 1 gram tert.-butyl chloride in 1300 grams of reformate, also pumped at 76 ml/hr. Simultaneously with this charge, 10 ml/hr of charge naphtha was begun and the rate was increased 15 ml/hr at 20 minute intervals to 100 ml/hr. After this was attained, the rate of promoter II was decreased to 7.5 ml/hr and the charge naphtha was increased to 145 ml/hr. Following this adjustment, promoter II was replaced with a solution containing 1500 cc of naphtha and 30 cc of 1% tert.-butyl chloride in naphtha. The catalyst was then on stream and subsequently adjusted to operating conditions.

EXAMPLE 4

The catalyst of Example 4 was prepared by mixing equal amounts by weight of 0.6% platinum and 0.2% iridium-containing 1/16 inch gamma-alumina beads. This resulted in an overall compositions of 0.3% platinum and 0.1% iridium. The components were prepared by impregnating the beads with aqueous $H_2PtCl_6$ or $H_2IrCl_6$ solutions. The platinum catalyst was dried for one hour at 950° F. in air and the iridium catalyst was dried for one hour at 700° F. in nitrogen.

EXAMPLE 5

The catalyst of Example 4 was presulfided at 750° F. with gas containing 400 ppm of hydrogen sulfide in hydrogen. The catalyst was distributed as follows: 12 grams in the first reactor, 22 grams in the second reactor and 25 grams in the last reactor. The presulfiding gas was first introduced into the top of the last reactor at 2 standard cubic feet per hour. Addition was contained until the breakthrough of $H_2S$ was detected after the last reactor. When breakthrough occurred, $H_2S$ addition was stopped and the amount of gas was noted (2.269 cu. ft.). The first and second reactor were similarly presulfided in series. Two standard cubic feet per hour of presulfiding gas were introduced into the first reactor while breakthrough was monitored between the second and last reactor. When breakthrough occurred (1.547 cu. ft.), the presulfiding gas addition was stopped.

The catalyst was then streamed with 33.3 ml of a solution containing charge naphtha with 1% tert.-butyl chloride. This was followed by charge naphtha along with a solution containing 1500 cc of naphtha and 30 cc of 1% tert.-butyl chloride in naphtha resulting in 1-10 ppm chloride being added.

EXAMPLE 6

The catalyst of Example 4 was pretreated at 650° F., 100 psig and a recycle of 10 standard cubic feet per hour with 98 R+O reformate. The catalyst was loaded by placing 12 grams in the first reactor, 22 grams in the second reactor and 25 grams in the last reactor. The catalyst was initially pretreated by adding 33.3 ml of a solution composed of 130 grams of reformate and 1 gram tert.-butyl chloride. This was followed by the addition of a solution (Promoter II) composed of 1300 grams of reformate and 1 gram of tert.-butyl chloride charged at 100 ml/hr. Simultaneously, the addition of 10 ml/hr of charge naphtha was begun and the rate was increased 15 ml/hr at 20 minute intervals to a final rate of 100 ml/hr. After this was attained, the rate of addition of Promoter II was decreased to 10 ml/hr and the rate of charge naphtha was increased to 190 ml/hr. Promoter II, containing reformate, was then replaced by a solution containing 1500 cc of naphtha and 30 cc of 1% tert.-butyl chloride in naphtha and the catalyst was on stream.

Reforming of $C_6$-330° F. Arab Light Naphtha was accomplished in a adiabatic pre-reactor system at a pressure of 200 psig, a recycle mole ratio of hydrogen to charge of 5 and a weight hourly space velocity of 2.5.

Figure 2:
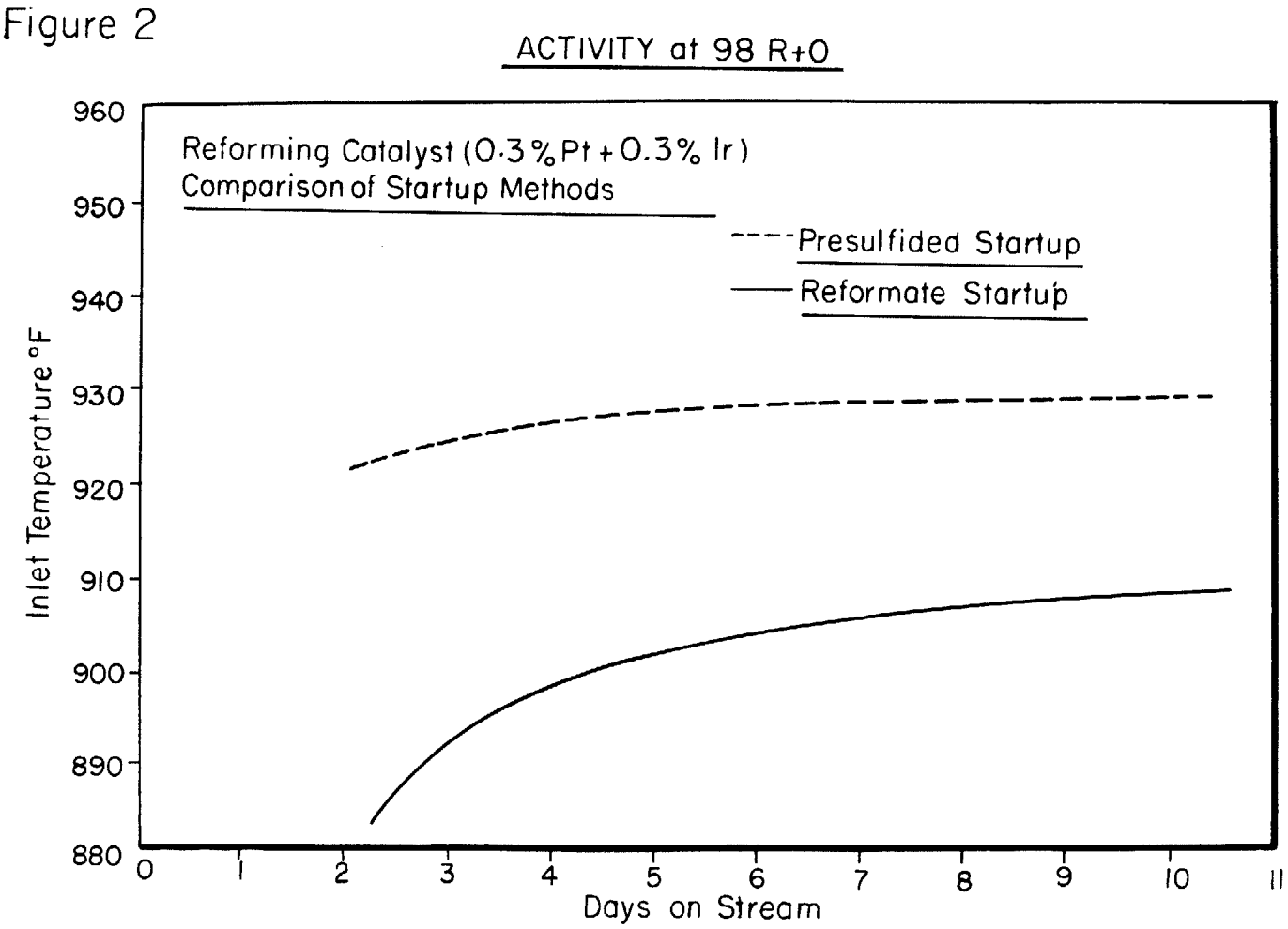
FIGS. 2 and 3 depict data showing comparison of startup methods utilizing the technique of the present invention with previously employed conventional presulfiding.
Figure 3:
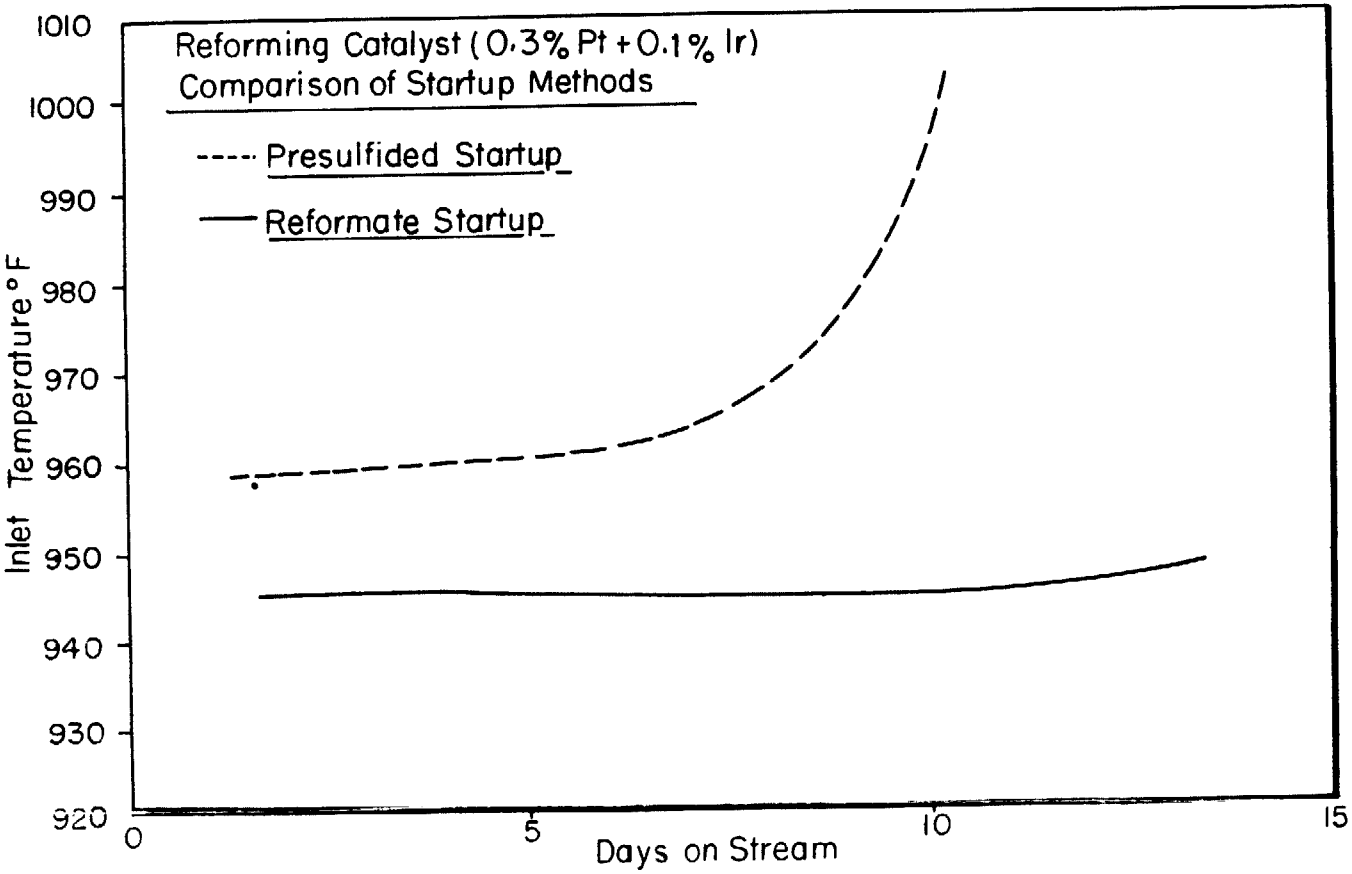

The results obtained are shown graphically in FIGS. 2 and 3 where inlet temperature necessary to obtain a product having an octane number of 98 R+O is plotted against time on stream. Comparative results obtained using the catalyst of Example 1 wherein a presulfided start up and a reformate start up are shown in FIG. 2. After the start up both the presulfided and reformate treated catalyst were run identically. It will be seen from the results presented graphically in FIG. 2 that the amount of activity gained due to the reformate start up was approximately 20° F.

Comparative results obtained using the catalyst of Example 4 in a presulfided start up and in a reformate start up are shown in FIG. 3. Referring more particularly to the results presented graphically in the latter Figure, it will be seen that the catalyst which was presulfided was unable to recover with the iridium level at 0.1%. Such result is presumably due to the rapid rate of coking on the platinum sites. The catalyst which was started up with reformate treatment, on the other hand, without presulfiding, lined out between 945°-950° F. Such level of activity is presumed due to the iridium concentration of 0.1%.

It is to be understood that the above description is merely illustrative of preferred embodiments of the invention, of which many variations may be made within the scope of the following claims by those skilled in the art without departing from the spirit thereof.

What is claimed is:

1. In a process for reforming a hydrocarbon charge under reforming conditions in the presence of a [sulfur-sensitive metal-containing reforming catalyst] *reforming catalyst selected from the group consisting of platinum, platinum and iridium or platinum, iridium and rhenium,* in a reforming zone, wherein said charge conducted to said reforming zone contacts said catalyst in an initial or [freshy] *freshly* regenerated state giving rise to over-cracking of said charge with concomitant loss in activity thereof and excessive temperature rise in said zone, the improvement which comprises pre-treating said catalyst prior to contact with said charge by passing thereover a reformate characterized by an octane number (R+O) of between about 90 and about 100, [and] an aromatics content within the approximate range of 40 to 50 mole percent *and sulfur content up to 10 ppm* for a period of time, generally at least about 0.5 hour and no more than about 3 hours at a temperature between about 600° F. and about 750° F., thereby substantially suppressing the adverse effects of said over-cracking and excessive temperature rise.

2. The process of claim 1 wherein said temperature is between 650° F. and about 700° F.

3. The process of claim 1 wherein said period of time is [generally] at least about 1 hour and no more than about 3 hours.

[4. The process of claim 1 wherein said reforming catalyst is a multimetallic catalyst comprising platinum in combination with rhenium and/or iridium deposited on a refractory support.]

5. The process of claim 1 wherein said catalyst comprises platinum and iridium deposited on a refractory support.

[6. The process of claim 1 wherein said catalyst comprises platinum and rhenium deposited on a refractory support.]

7. The process of claim 1, wherein said catalyst comprises a minor proportion of platinum deposited on a refractory support and a minor proportion of iridium [deposted] *deposited* on a separate support.

8. The process of claim 1 wherein said catalyst comprises a minor proportion of platinum and rhenium deposited on a refractory support and a mimor proportion [or] *of* iridium deposited on a separate support.

[9. The process of claim 4 wherein said support is alumina.]

10. The process of claim 5 wherein said support is alumina.

[11. The process of claim 6 wherein said support is alumina.]

12. The process of claim 7 wherein said support is alumina.

13. The process of claim 8 wherein said support is alumina.

14. The process of claim 1 wherein said hydrocarbon charge is a petroleum naphtha.

15. The process of claim 1 wherein said reformate constitutes at least in part a recycle stream of the reformate product produced in said reforming zone.

[16. The process of claim 1 wherein said reformate contains a small amount of sulfur, not exceeding about 10 ppm.]

17. The process of [claim 16] *claims 1, 2, 3, 10, 12, 13, or 15* wherein said charge initially contains between about 2 and about 10 ppm of sulfur and said catalyst is exposed thereto for a period of time within the approximate range of 5 to 24 hours, after which the catalyst is contacted with the charge of lower sulfur content.

*18. The process of claim 17 wherein said charge initially contains about 4 to about 8 ppm of sulfur.*

*19. The process of claim 18 wherein said charge of lower sulfur content contains 2 ppm or less of sulfur.*

*20. The process of claim 1 wherein said catalyst comprises platinum.*

*21. The process of claim 20 wherein said catalyst additionally comprises a halogen component.*

*22. The process of claim 21 wherein the platinum content of the catalyst is about 0.01 to about 3 percent, based on the weight of the catalyst, and the halogen content of the overall catalyst is about 0.1 to about 5 weight percent.*

*23. The process of claim 22 wherein said halogen is chlorine, bromine or fluorine.*

*24. The process of claim 23 wherein said halogen is chlorine.*

*25. The process of claims 10 or 12 wherein said catalyst additionally comprises a halogen component.*

*26. The process of claim 25 wherein the platinum content of said catalyst is about 0.01 to about 3 percent, based on the weight of the catalyst, the iridium content of said catalyst is about 0.01 to about 3 percent, based on the weight of the catalyst, and the halogen content of the overall catalyst is about 0.1 to about 5 weight percent.*

*27. The process of claim 26 wherein said halogen is chlorine, bromine or fluorine.*

*28. The process of claim 27 wherein said halogen is chlorine.*

*29. The process of claim 13 wherein said catalyst additionally comprises a halogen component.*

*30. The process of claim 29 wherein the platinum content of said catalyst is about 0.01 to about 3 percent, based on the weight of the catalyst, the iridium content of said catalyst is about 0.01 to about 3 percent, based on the weight of the catalyst, the rhenium content of said catalyst is about 0.01 to about 3 percent, based on the weight of the catalyst, and the halogen content of the overall catalyst is about 0.01 to about 5 weight percent.*

*31. The process of claim 30 wherein said halogen is chlorine, bromine or fluorine.*

*32. The process of claim 31 wherein said halogen is chlorine.*

* * * * *